(12) United States Patent  
Herve

(10) Patent No.: US 9,198,574 B1  
(45) Date of Patent: Dec. 1, 2015

(54) EYE EXAMINATION AID

(71) Applicant: Don J Herve, Andover, MN (US)

(72) Inventor: Don J Herve, Andover, MN (US)

(*) Notice: Subject to any disclaimer, the term of this patent is extended or adjusted under 35 U.S.C. 154(b) by 423 days.

(21) Appl. No.: 13/659,251

(22) Filed: Oct. 24, 2012

Related U.S. Application Data

(60) Provisional application No. 61/567,339, filed on Dec. 6, 2011.

(51) Int. Cl.
*A61B 3/10* (2006.01)
*A61B 3/00* (2006.01)
*A61B 3/14* (2006.01)
*A61B 3/02* (2006.01)
*A61B 3/103* (2006.01)
*A61B 3/12* (2006.01)

(52) U.S. Cl.
CPC .............. *A61B 3/103* (2013.01); *A61B 3/1225* (2013.01)

(58) Field of Classification Search
CPC ........ A61B 3/1225; A61B 3/12; A61B 3/103; A61B 3/14; A61B 3/133; A61B 3/1015
USPC ......... 351/200, 205–206, 208–211, 216–218, 351/221–223, 233–235, 239–240, 243, 351/245–246
See application file for complete search history.

(56) References Cited

U.S. PATENT DOCUMENTS

| | | | |
|---|---|---|---|
| 5,319,399 A | 6/1994 | Hudgins | |
| 5,812,241 A | 9/1998 | Doms et al. | |
| 5,883,693 A | 3/1999 | Iki | |
| 5,929,972 A | 7/1999 | Hutchinson | |
| 6,497,483 B2 | 12/2002 | Frey et al. | |
| 2003/0216763 A1* | 11/2003 | Patel | 606/166 |
| 2003/0218880 A1* | 11/2003 | Brukilacchio | 362/293 |
| 2008/0123054 A1 | 5/2008 | Humber | |
| 2009/0103050 A1* | 4/2009 | Michaels et al. | 351/208 |

* cited by examiner

*Primary Examiner* — Dawayne A Pinkney
(74) *Attorney, Agent, or Firm* — Patterson Thuente Pedersen, P.A.

(57) ABSTRACT

An eye examination aid including an aligner/illuminator and a mount. The aligner/illuminator includes a first body containing a visible light laser and an illumination source emitting non-coherent light. The visible light laser has a laser axis along which visible laser light is emitted. The mount includes a second body having a receiving portion into which the aligner/illuminator is removably receivable in a fixed orientation and presenting a first generally planar side oriented substantially parallel to the laser axis and a second generally planar side oriented substantially perpendicular to the laser axis. At least one of the first generally planar side and the second generally planar side are structured to receive an adhesive whereby the mount is adapted to be secured to an external surface of a refractor instrument such that the laser axis is directed substantially parallel to an optical axis of the refractor instrument.

21 Claims, 7 Drawing Sheets

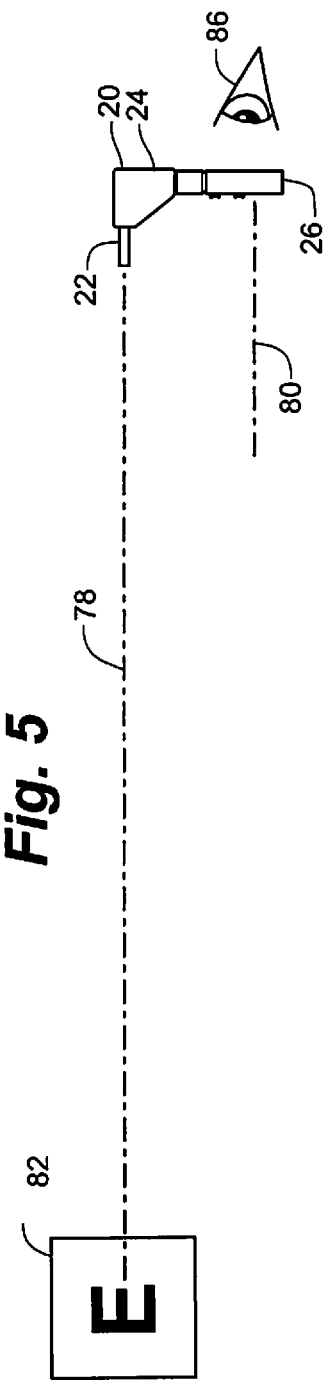
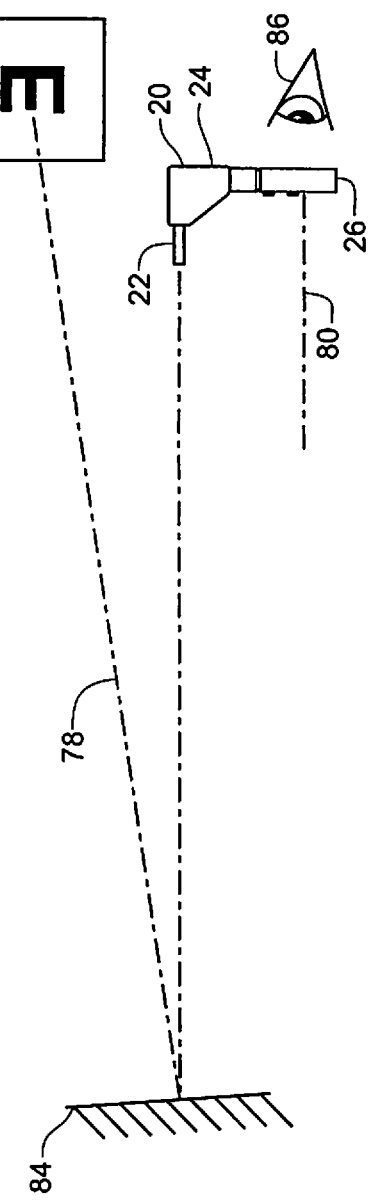

EYE EXAMINATION AID

RELATED APPLICATION

The present application claims the benefit of U.S. Provisional Application No. 61/567,339 entitled "Eye Examination Aid" filed Dec. 6, 2011, which is incorporated herein in its entirety by reference.

FIELD OF THE INVENTION

The invention relates generally to instruments used in examination of the eyes to determine refractive error. More particularly, the invention relates to an aid for use with a phoropter or refractor.

BACKGROUND OF THE INVENTION

Phoropters or refractors are instruments that are used in the eye examination process to assist in determining refractive error during what is called subjective examination. That is, where the eye examiner presents various tests and images viewed through the phoropter or refractor to a patient who makes subjective responses to questions asked by the eye examiner. The eye examiner then makes judgment based on the subjective responses of the patient to alter the prescription until a desired refractive prescription is obtained.

Eye examination generally occurs in darkened rooms because the eye chart and other testing images are typically projected onto a screen for viewing by the patient or more recently presented on a computer monitor. At one time, eye examination rooms were typically made about 24 feet long to permit projection of an eye chart or other testing images approximately 20 feet from the eyes of the patient being examined. Twenty feet or six meters is considered to be optical infinity. That is, a distance great enough that a refractive result obtained at optical infinity is insignificantly different from the refractive correction that would be required for viewing objects at actual infinity. More commonly these days, exam rooms are shorter than 24 feet and the patient views an image of the eye chart reflected in mirror at the end of the room, the projected eye chart is actually positioned behind the patient and above their head. Commonly, the eye chart is projected by a projector onto a second mirror that is then reflected back to the back wall of the examination room on a screen which is then viewed by the patient in the first mirror. While some refractors manufactured in recent years incorporate some sort of illumination built into the instrument to aid the Examiner in seeing the settings and registrations of the instrument. The vast majority of refractors presently in use do not include any sort of illumination.

It can be difficult to properly align the patient so that the patient looking through the refractor has their line of sight and that of the refractor directed at the mirror on the far wall of the examination room and properly seeing the eye chart which is presented on the wall behind the patient being examined.

During some kinds of testing done during an eye examination, ultraviolet or deep blue near ultraviolet light is used as an excitation wavelength of light to excite the fluorescence of a chemical substance called fluoroscien. Fluoroscien is a fluorescent dye agent that may be instilled into the eyes in the form of eye drops or by dry filter paper strips impregnated with Fluoroscien in order to assist in the diagnosis of problems with the ocular tear film or increase the visibility of injuries or dry spots on the surface of the eye or ocular adnexa. Fluoroscien may be excited to fluoscence by the application of ultraviolet light from an ultraviolet fluorescent tube or by the direction of high intensity visible light through a cobalt blue filter or by another source of ultraviolet light or near ultraviolet deep blue light.

In a darkened eye examination room, it can be difficult to align the phoropter or refractor so that the patient is looking through it directly at and sees the distant eye chart. This is especially difficult if the patient has poor verbal capabilities. It can also be difficult to view non-illuminated markings or indicia on the phoropter or refractor or other instruments used in the eye examination process.

There still is room for improvement in instrumentation in the eye examination arts.

SUMMARY OF THE INVENTION

The invention solves many of the above discussed problems. The eye examination aid of the present invention generally includes an aligner/illuminator and a mount to be used in cooperation with a phoropter or refractor. The aligner/illuminator of the invention generally includes a visible laser similar to that used in a laser pointer and an illumination source which emits light in visible and/or ultraviolet wavelengths. The mount according to the invention, is adapted to be secured to an existing phoropter or refractor that is commonly used to determine refractive error in patients.

According to an example embodiment of the present invention, the aligner/illuminator includes a generally cylindrical body defining two openings on a circular end thereof through which laser light and ultraviolet or visible illumination light pass respectively. At an opposing end from the two openings may be located a permanent magnet that is usable to secure the aligner/illuminator to the mount. Thus, the aligner/illuminator is secured to the mount with accurate alignment to the phoropter but also readily removable for other uses and replaceable.

The aligner/illuminator is battery powered according to one embodiment of the present invention. The aligner/illuminator may also be equipped with contacts to allow it to be connected via the mount to an electrical source for battery recharging.

The mount, according to one embodiment of the invention, may have generally the shape of an irregular pentagonal prism. The mount may include four sides that are oriented at generally right angles to one another and a fifth side that is oriented at an angle other than a right angle to the other sides. According to one embodiment of the present invention, the mount includes a generally cylindrical cavity therein which is dimensioned to receive the aligner/illuminator therein. A second permanent magnet or piece of ferrous metal is secured at the circular end of the cavity.

According to one embodiment of the present invention, two of the sides of the mount are particularly adapted to be, for example, adhesively secured to portions of a standard phoropter or refractor to secure the aligner/illuminator in an orientation generally perpendicular to the front face of the phoropter and, in particular, in parallel alignment with the line of sight of the phoropter or refractor instrument.

According to another embodiment of the invention, the aligner/illuminator is oriented so that the visible laser beam is initially directed substantially perpendicular to the optical axis of the existing phoropter or refractor and deflected, for example by a mirror or prism, to be parallel to the optical axis of the existing phoropter or refractor. In this embodiment the mount is secured to the phoropter or refractor such that the visible laser beam is initially directed substantially perpendicular to the optical axis of the existing phoropter or refractor. In an example according to this embodiment the mount defines a passage in which the aligner/illuminator is positioned such that the visible laser beam is directed into the mount and reflected from a mirror or prism internally located in the mount. The mirror or prism can be oriented at a forty five degree angle so that the visible laser beam is directed parallel to the optical axis of the phoropter or refractor.

According to another example embodiment, the aligner/illuminator is oriented so that the visible laser beam intersects the line of sight of the phoropter or refractor at a selected distance. The selected distance can be equal to the distance at which an eye chart or testing target is presented to the patient.

In use, the mount is secured to the phoropter or refractor for example, by the use of a permanent adhesive such as a double sided foam adhesive mounting tape. Alternately, the mount may be secured to the phoropter or refractor by securing a permanent magnet to one of the mount or the phoropter or refractor and a piece of ferrous metal to the other if the refractor is not made of ferrous metal.

In operation, when it is desired to align the phoropter or refractor appropriately with an eye chart distantly located from the phoropter or refractor, the examining health professional activates the visible laser of the aligner/illuminator. The health professional can then adjust the position of the phoropter or refractor until the visible laser spot is located in the center of the distant eye chart. Once alignment is achieved, the phoropter or refractor is secured in that position and the illumination of the laser is switched off.

When it is desired to use the aligner/illuminator to illuminate some part of the examining equipment or the patient's eye, the aligner/illuminator is removed from the mount and hand held by the examining health professional who can then direct visible and/or ultraviolet light or near ultraviolet light toward the instrumentation or the patient's eye. In another use of the present invention, when an ultraviolet fluorescent dye such as fluorescien is instilled into the patient's eye, the aligner/illuminator may be used to direct ultraviolet light or near ultraviolet light toward the patient's eye thus creating fluorescence of the fluorescien and a highly visible illumination of the tear layer as well as any abrasions of the cornea or conjunctive that may exist. When the examining health professional is done using the aligner/illuminator it can be return to its position in the mount where the aligner/illuminator is held securely in place by the permanent magnet or other securing mechanism.

The present invention also includes a method of aligning a phoropter or refractor with a distant eye chart. The method including securing a mounting to the phoropter or refractor so that the aligner/illuminator emits a visible laser beam that is ultimately oriented substantially parallel to the line of sight of the phoropter or refractor. The visible laser beam may be emitted from the aligner illuminator parallel to the optical axis of the photpter because the aligner/illuminator is oriented parallel to the optical axis of the phoropter or refractor or the visible laser beam may initially be emitted in a direction non-parallel to the optical axis of the phoropter or refractor and redirected to be substantially parallel to the optical axis of the phoropter or refractor. Redirection may be accomplished by deflection of the visible laser beam from a mirror or prism. Thus, the ultimate visible laser axis is the axis upon which the visible laser beam travels upon leaving the combination of the laser aligner/illuminator and the mount when the laser aligner/illuminator is positioned in the mount. The method further includes illuminating the aligner/illuminator so that the visible laser that is directed substantially parallel to the optical axis of the phoropter or refractor and centering the laser spot on a distant eye chart. The laser is then turned off and the refractive examination can continue as is usually done.

The method may also include orienting the aligner/illuminator so that the visible laser that is directed substantially perpendicular to the optical axis of the phoropter or refractor and deflected by, for example a mirror or prism, to be generally parallel to the optical axis of the phoropter or refractor.

BRIEF DESCRIPTION OF THE DRAWINGS

FIG. 5 is a schematic perspective view of a refractor with an examination aid mounted thereon depicting alignment with an eye chart in accordance with an example embodiment of the invention;

FIG. 6 is a schematic perspective view of a refractor with an examination aid mounted thereon depicting alignment with an eye chart via a mirror in accordance with an example embodiment of the invention;

DETAILED DESCRIPTION

Figure 1:
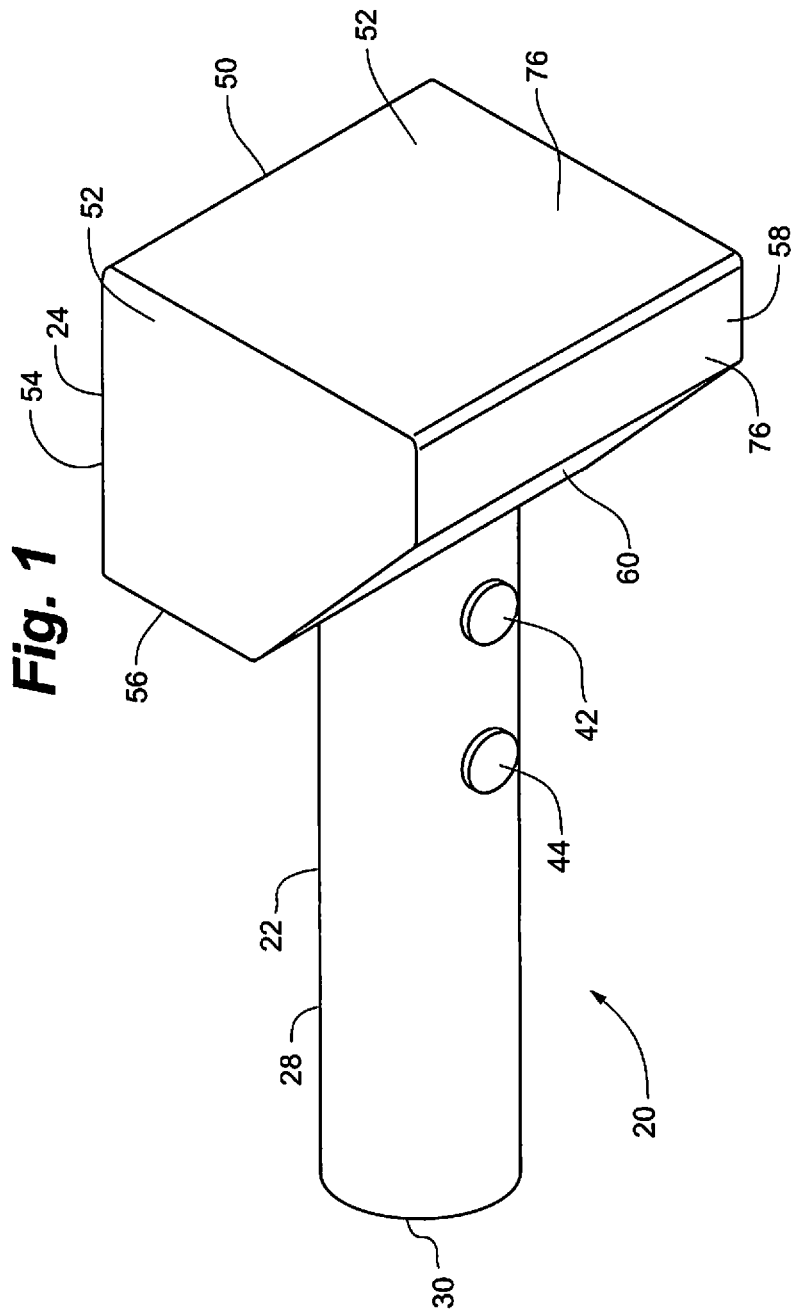
FIG. 1 is a perspective view of an examination aid according to an example embodiment of the present invention.
Figure 2:
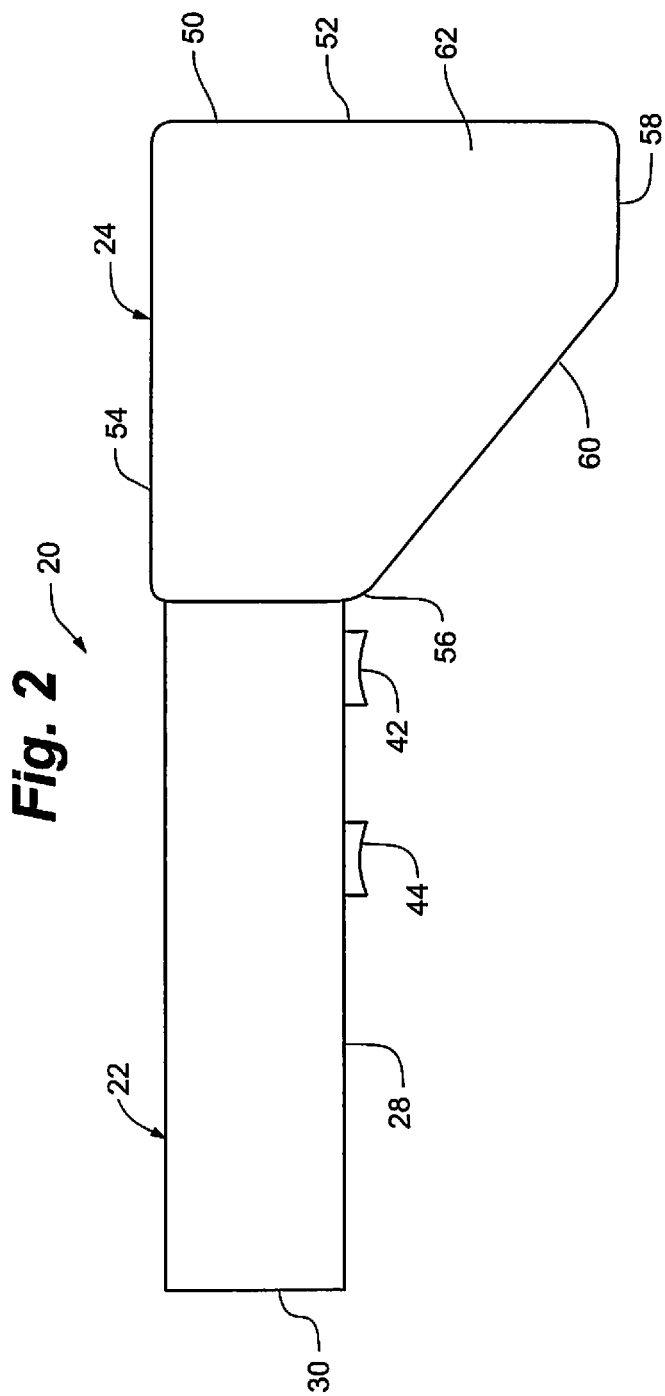
FIG. 2 is a side elevational view of the examination aid of FIG. 1.
Figure 3:
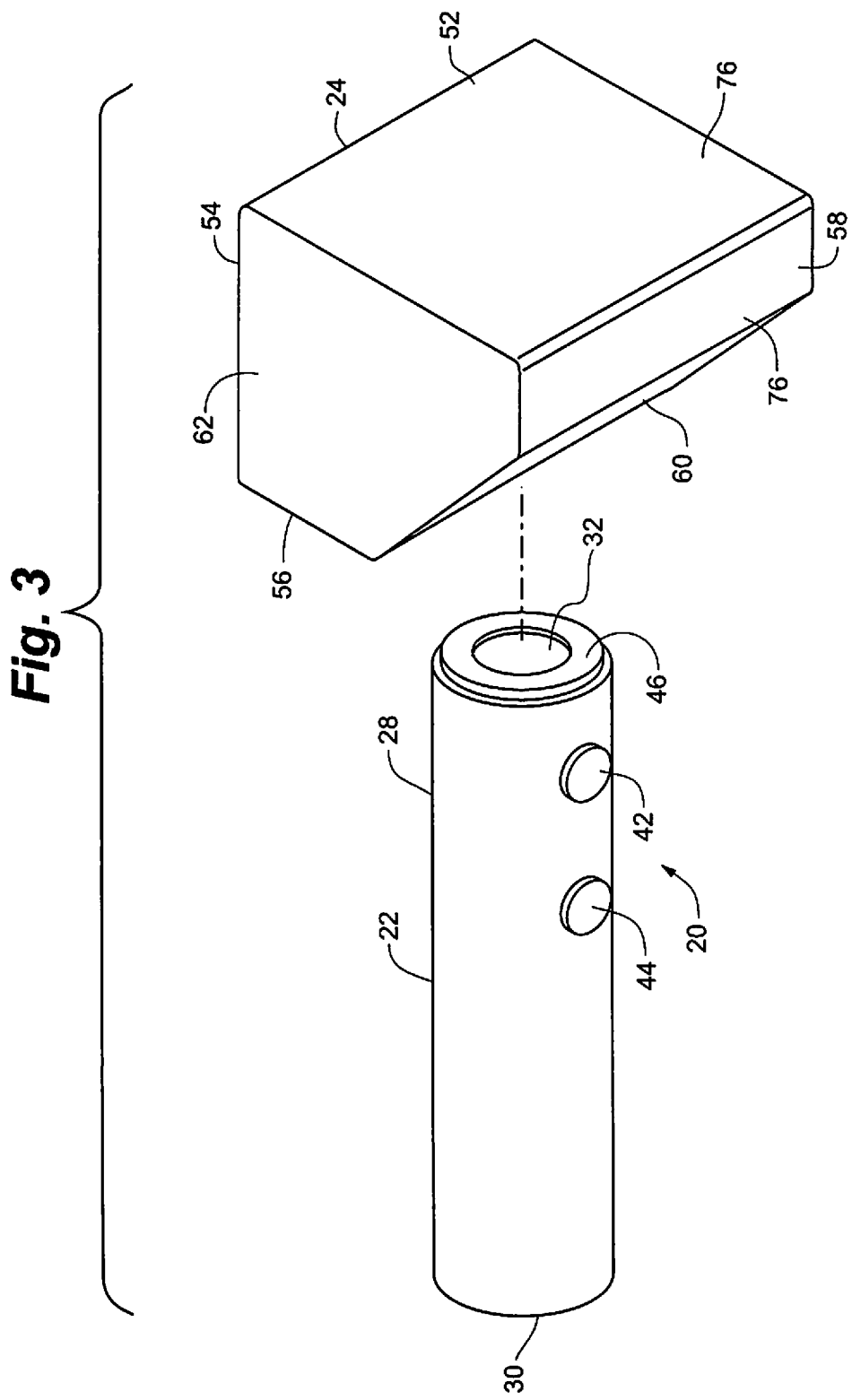
FIG. 3 depicts the examination aid according to an example embodiment of the invention with the mount separated from the aligner/illuminator.

Referring to FIGS. 1-4 and 7, eye examination aid 20, according to an example embodiment of the invention, generally includes aligner/illuminator 22 and mount 24. Mount 24 is adapted to secure eye examination aid 20 to a surface of phoropter or refractor 26.

Referring particularly to FIGS. 1-3 and 7, in the depicted example embodiment aligner/illuminator 22 generally includes cylindrical body 28 having front end 30 and rear end 32. Cylindrical body 28 houses visible laser 34 and illumination source 36. Front end 30 presents laser aperture 38 and illumination aperture 40. Visible laser 34 is positioned and oriented so that a generated laser beam passes through laser aperture 38. Illumination source 36 is positioned so that its illumination passes through illumination aperture 40.

Cylindrical body 28 also presents laser switch 42 and illumination switch 44. Laser switch 42 is coupled to visible laser 34 and permits visible laser 34 to be illuminated. Illumination switch 44 is coupled to illumination source 36 and permits illumination source 36 to be turn on or off. Laser switch 42 and illumination switch 44 may be, for example, momentary contact switches. Rear end 32 of cylindrical body 28 may include permanent magnet 46. Cylindrical body 28 may be separatable into at least two parts for battery changing and the like.

Cylindrical body 28 may also present, in one example embodiment, battery charger electrical contacts 48.

Referring to FIGS. 1-3 and 4, mount 24, according to an example embodiment, generally includes pentagonal body 50. Pentagonal body 50 presents back 52, top 54, front 56, bottom 58, angled side 60 and pentagonal sides 62.

Figure 4:
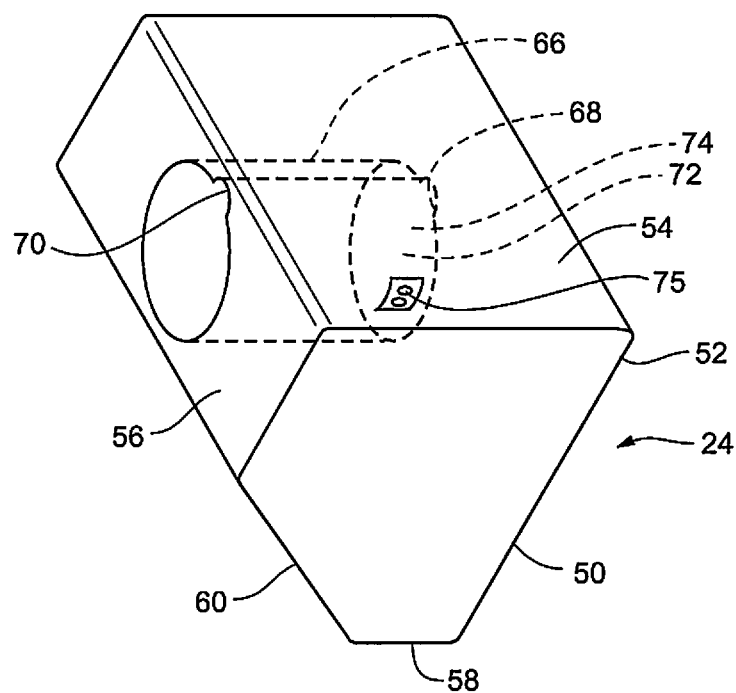
FIG. 4 is a perspective view of a mount according to an example embodiment of the invention with some structures depicted in phantom.
Figure 7:
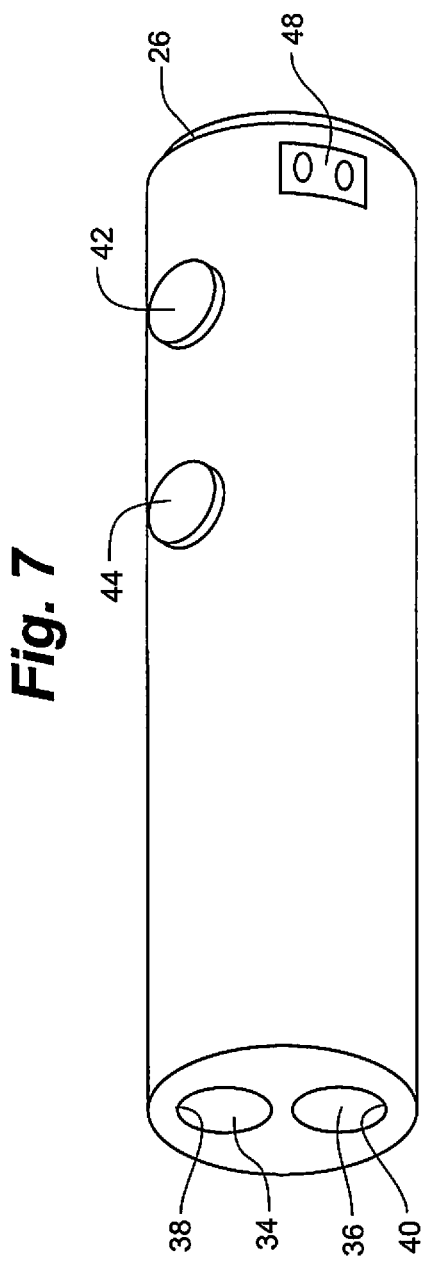
FIG. 7 is a perspective view of an aligner/illuminator according to an example embodiment of the invention.

In the embodiment as depicted in FIG. 4, pentagonal body 50 defines cylindrical cavity 64 that extends into front 56. Cylindrical cavity 64 is bounded by cylindrical wall 66 and circular wall 68. Cylindrical wall 66 may include alignment groove 70. Circular wall 68 may support internal magnet 72 or alternately ferrous disk 74. Cylindrical cavity 64 may also present charging contacts 75

Pentagonal body 50 may support adhesive 76 on bottom 58, back 52 or top 54. Adhesive 76 may include a double sided adhesive tape or another contact adhesive. Pentagonal body 50 may also be secured to phoropter or refractor by other means known to those of skill in the art including but not limited to magnets or brackets.

Referring to FIGS. 5 and 6, the invention also includes a method of aligning a preexisting phoropter or refractor 26 including securing mount 24 to a surface of phoropter or refractor 26. The method further includes inserting aligner/illuminator 22 including visible laser 34 and illumination source 36 mount 24 such that aligner/illuminator 22 is removably received in mount 24 in a fixed orientation. The method further includes illuminating visible laser 34 of aligner/illuminator 22 such that visible laser 34 emits visible light laser beam 78 substantially parallel to an optical axis 80 of phoropter or refractor 26. The method includes movably adjusting a position of the phoropter or refractor 26 until visible light laser beam 78 strikes a desired preselected distant target such as eye chart 82. The method then includes securing phoropter or refractor 26 in the position wherein the visible light laser beam 78 strikes eye chart 82. Phoropter or refractor 26 is the aligned so that patient's eye 86 can see eye chart 82 generally centered in the field of view of phoropter or refractor 26.

In another embodiment the method includes reflecting visible light laser beam 78 from mirror 84 to eye chart 82.

The method may further include removing aligner/illuminator 22 from mount 24 and directing emitted non-coherent light toward refractor or phoropter 26 or another instrument to assist in reading indicia on refractor or phoropter 26 or the other instrument.

The method may further include applying a fluorescent dye agent to patient's eye 86, removing aligner/illuminator 22 from mount 24 and directing the emitted non-coherent light toward the patient's eye whereby the fluorescent dye agent is excited to fluorescence.

Figure 9:
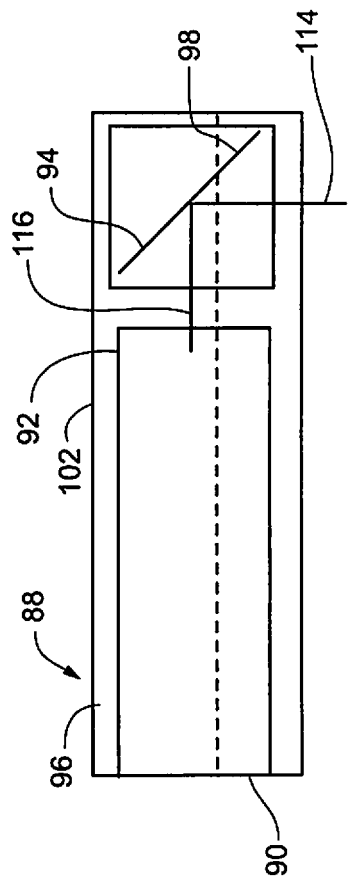
FIG. 9 is a plan view of the embodiment of the examination aid depicted in FIG. 8.
Figure 10:
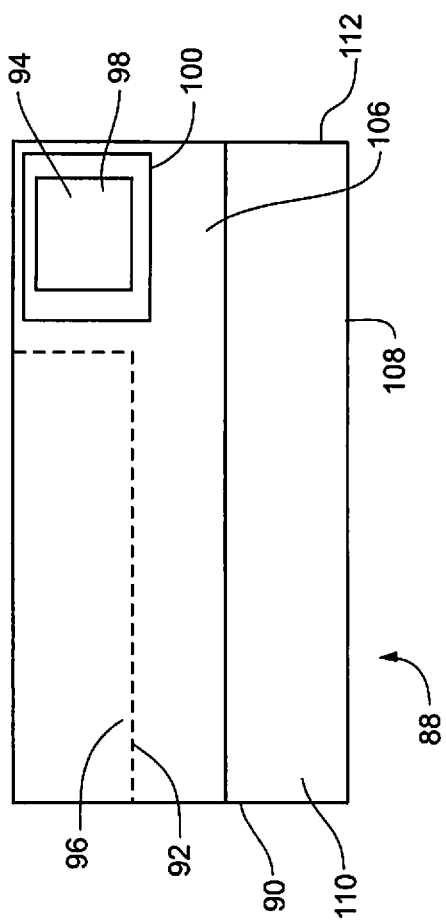
FIG. 10 is a front elevational view of the embodiment of the examination aid depicted in FIG. 8.
Figure 8:
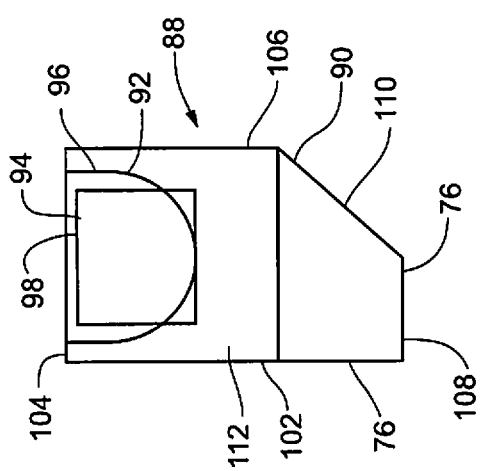
FIG. 8 is a side elevational view of another embodiment of the examination aid according to an example embodiment of the invention.

Referring to FIGS. 8-10, according to another embodiment of the invention, eye examination aid 20 includes deflecting mount 88 structured to support aligner/illuminator 22. Deflecting mount 88 generally includes a unitary body 90 defining aligner/illuminator receiver 92 and optical deflector 94. Aligner/illuminator receiver 92 includes cradle 96 which is shaped and dimensioned to receive aligner/illuminator 22 therein with illumination aperture 36 and laser aperture 38 facing optical deflector 94.

Optical deflector 94 may include mirror 98 or a prism (not shown but known to those of skill in the art) and is oriented, for example, at a forty five degree angle to visible light laser beam 78 as it exits laser aperture 38.

Deflecting mount 88 may also include window 100 in front of mirror 98 that protects mirror 98 from dust and contamination.

Deflecting mount 88 generally presents back 102, top 104, front 106, bottom 108, angled side 110 and generally pentagonal sides 112. Cradle 96 can be open at the top as depicted in FIGS. 9 and 10 or closed at the top as depicted in FIG. 8. In one example embodiment of defecting mount 88 ultimate laser axis 114 is oriented at a right angle to aligner/illuminator laser axis 116.

In the case of mount 24 ultimate laser axis 114 is coincident with aligner/illuminator laser axis 116.

In operation, eye examination aid 20 is secured to phoropter or refractor 26 by mount 24. Mount 24 can be adhesively or otherwise secured to phoropter or refractor 26 so that the visible laser 34 of aligner/illuminator 22 is aligned substantially parallel to the line of sight of phoropter or refractor 26. For example, bottom 58 of pentagonal body 50 of mount 24 may be secured to a top planar surface of phoropter or refractor 26. Alternately, back 52 of mount 24 may be secured to a front surface of phoropter or refractor 26.

When it is desired to align phoropter or refractor 26 so that the patient behind phoropter or refractor 26 is viewing a distant eye chart, visible laser 34 is actuated and phoropter or refractor 26 is adjusted until the spot of visible laser 34 is visible centrally on the distant eye chart.

When it is desired to use the illumination function of aligner/illuminator 22, the health professional removes the aligner/illuminator 22 from mount 24 and activates illumination source 36 via illumination switch 44. The health professional may then direct visible or ultra violet or near ultra violet light onto the instrument to read indicia that may be difficult to see in the darkened eye examination room or may utilized the illumination source to illuminate fluoroscien or another fluorescent dye that may be applied to the tear film and/or ocular structures of the patient. Permanent magnet 46 in combination with internal magnet 72 or ferrous disk 74 allows ready removal of aligner/illuminator 22 from mount 24 as well as ready return and storage of aligner/illuminator 22 in mount 24.

Mount 24 can be manufactured using a three axis CNC milling machine or by molding or other machining processes. Eye examination aid 20 eliminates the need for subjective feedback from the patient and provides good optical alignment of the phoropter with the distant eye chart in the darken environment of a common eye examination room.

According to the embodiment depicted in FIGS. 8-10, eye examination aid 20 is structured so that visible laser beam 78 is initially directed substantially perpendicular to optical axis 80 of existing phoropter or refractor 26 and deflected by optical deflector 94 to be parallel to optical axis 80 of existing phoropter or refractor 26. In this embodiment deflecting mount 88 is secured to phoropter or refractor 26 such that visible light laser beam 78 is initially directed substantially perpendicular to optical axis 80 of existing phoropter or refractor 26 and deflected to be parallel to optical axis 80 of phoropter or refractor 26.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

The invention claimed is:

1. An eye examination aid, comprising:
   an aligner/illuminator including a first body having therein a visible light laser and an illumination source emitting non-coherent light, the visible light laser having an aligner/illuminator laser axis along which visible laser light is emitted;
   a mount including a second body having a receiving portion into which the aligner/illuminator is removably receivable in a fixed orientation, the mount presenting a first generally planar side oriented substantially parallel to the laser axis and a second generally planar side oriented substantially perpendicular to the laser axis; and at least one of the first generally planar side and the second generally planar side being structured to receive an adhesive whereby the mount is adapted to be secured to an external surface of a refractor instrument such that an ultimate laser axis is directed substantially parallel to an optical axis of the refractor instrument or such that the ultimate laser axis intersects the optical axis of the refractor instrument at a preselected distance from the refractor instrument.

2. The eye examination aid as claimed in claim 1, wherein the first body is generally cylindrical and the receiving portion comprises a generally cylindrical cavity in the second body.

3. The eye examination aid as claimed in claim 1, wherein the second body comprises a generally pentagonal prism defining a generally cylindrical cavity in a front face thereof.

4. The eye examination aid as claimed in claim 1, wherein the non-coherent light is emitted in a visible light wavelength.

5. The eye examination aid as claimed in claim 1, wherein the non-coherent light is emitted in an ultraviolet or near ultraviolet light wavelength.

6. The eye examination aid as claimed in claim 1, wherein the visible light laser and the illumination source emitting non-coherent light are each coupled to a respective momentary contact switch by which the visible light laser and the illumination source emitting non-coherent light are each individually activateable.

7. The eye examination aid as claimed in claim 1, wherein the illumination source emitting non-coherent light comprises a light emitting diode.

8. The eye examination aid as claimed in claim 1, further comprising a magnet coupled to one of the aligner/illuminator or the mount.

9. The eye examination aid as claimed in claim 1, further comprising adhesive applied to the first generally planar side.

10. The eye examination aid as claimed in claim 1, further comprising adhesive applied to the second generally planar side.

11. The eye examination aid as claimed in claim 1, further comprising an optical deflector supported by the mount at an angle to the aligner/illuminator laser axis.

12. The eye examination aid as claimed in claim 11, wherein the aligner/illuminator laser axis is generally perpendicular to the ultimate laser axis.

13. A method of aligning a preexisting refractor, comprising:

securing a mount to a surface of the refractor;

inserting an aligner/illuminator including a visible laser and a source of non-coherent light into the mount such that the aligner/illuminator is removably received in the mount in a fixed orientation;

illuminating the visible light laser of the aligner/illuminator such that the visible light laser emits a visible light laser beam along an ultimate laser axis substantially parallel to an optical axis of the refractor;

movably adjusting a position of the refractor until the visible light laser beam strikes a desired preselected distant target; and securing the refractor in the position wherein the laser beam strikes the desired preselected distant target.

14. The method as claimed in claim 13, further comprising selecting the aligner/illuminator to emit non-coherent light in a visible light wavelength.

15. The method as claimed in claim 13, further comprising selecting the aligner/illuminator to emit non-coherent light in an ultraviolet or near ultraviolet light wavelength.

16. The method as claimed in claim 14, further comprising removing the aligner/illuminator from the mount and directing the emitted non-coherent light toward the refractor or another instrument to assist in reading indicia on the refractor or the other instrument.

17. The method as claimed in claim 15, further comprising applying a fluorescent dye agent to a patient's eye; removing the aligner/illuminator from the mount; and directing the emitted non-coherent light toward the patients eye whereby the fluorescent dye agent is excited to fluorescence.

18. The method as claimed in claim 14, further comprising securing the mount to the refractor with an adhesive.

19. The method as claimed in claim 18, further comprising applying the adhesive to a back surface of the mount that is substantially parallel to the laser axis.

20. The method as claimed in claim 18, further comprising applying the adhesive to a back surface of the mount that is substantially perpendicular to the laser axis.

21. The method as claimed in claim 13, further comprising directing the visible light laser beam along the aligner/illuminator laser axis to a deflector to be deflected such that the ultimate laser axis in generally perpendicular to the aligner/illuminator laser axis.

* * * * *